United States Patent [19]

Kirchhuebel

[11] Patent Number: 4,685,784
[45] Date of Patent: Aug. 11, 1987

[54] METHOD FOR CONTROLLING FIXATION OF A PATIENT'S EYE DURING PERIMETER MEASUREMENTS

[75] Inventor: Rainer Kirchhuebel, Wetzlar, Fed. Rep. of Germany

[73] Assignee: Oculus Optikgeraete GmbH, Wetzlar, Fed. Rep. of Germany

[21] Appl. No.: 777,399

[22] Filed: Sep. 18, 1985

[30] Foreign Application Priority Data

Sep. 19, 1984 [DE] Fed. Rep. of Germany ....... 3434319

[51] Int. Cl.⁴ ................................................ A61B 3/02
[52] U.S. Cl. .................................... 351/226; 351/225; 351/224
[58] Field of Search .................... 351/224, 225, 226

[56] References Cited

U.S. PATENT DOCUMENTS 3,718,386  2/1973  Lynn et al. ........................ 351/224
4,255,022  3/1981  Kuether et al. .................... 351/226

Primary Examiner—Rodney B. Bovernick
Attorney, Agent, or Firm—Flynn, Thiel, Boutell & Tanis

[57] ABSTRACT

A method for controlling the fixation of the eye of a patient during measuring of the sensitivity of the retina of the eye using a perimeter tester having a plurality of spaced testing light points of adjustable brightness, including the steps of adjusting the testing light point which lies in the center to the threshold value of the center of the eye of the patient, and thereafter repeatedly illuminating this testing light point with the threshold value or a super-threshold value near the threshold (1–4 dB superthreshold) to facilitate control of the fixation during the entire examination.

3 Claims, 2 Drawing Figures

METHOD FOR CONTROLLING FIXATION OF A PATIENT'S EYE DURING PERIMETER MEASUREMENTS

FIELD OF THE INVENTION

This invention relates to a method for controlling the fixation of a patient's eye, and in particular to a method of controlling fixation during measuring of the sensitivity of the retina of the eye with a perimeter testing device in which a plurality of spaced light points of adjustable brightness are offered to the patient's eye.

BACKGROUND OF THE INVENTION

Perimeter testers serve to measure the sensitivity of the retina of the human eye, wherein the sensitivity of the retina is reduced from the center toward the periphery. Thus, the testing point luminous density may by no means be the same all over the field of vision, but must be adjusted to the sensitivity curve of the tested eye. This is achieved in perimeter testers of the type in question here through a step-like gradation of the testing point luminous density.

Decisive for good results during the measuring of the sensitivity of the retina is a good fixation of the patient's eye on the centerpoint of the perimeter tester. This fixation must be maintained during all tests of the sensitivity, particularly during tests toward the periphery. It is known to have an observer constantly check the fixation through a telescope, which in the long run is tiresome. Furthermore, it is known to automatically check the fixation using an infrared transmitter and receiver system, wherein the corneal reflection of the patient is evaluated as a feedback signal. This infrared transmitter and receiver, however, sits exactly in the center of the perimeter ball in order to avoid reception of an oblique incident beam. The disadvantage of this arrangement is that the center of the retina cannot be examined directly, but only through an eccentric fixation, wherein then an automatic fixation control is no longer possible. Aside from these disadvantages, the system is also very susceptible to trouble, because a movement of the head without a change of the fixation leads to an error signal.

Furthermore, it is known to monitor the fixation by means of a television camera, wherein the pupil is adjusted directly with a curser. The smallest deviations can still be found here. This system is very precise, but is also very complicated and thus expensive.

A further known method for determining the fixation is to provide testing points in the blind spot, or in other words at the point at which the vision nerves enter the cortex. The disadvantage of this method is that the blind spot in individual patients is not always at exactly the same spot, and in addition can be of different sizes. This method can for this reason be used successfully only if, prior to the measurements, the blind spot is determined exactly in terms of position and size. This is, however, complicated, and on the other hand the limit values must then in addition be measured.

A basic purpose of the invention is thus to provide a method for testing the fixation of a patient's eye during perimeter measurements, which on the one hand, requires minimal testing effort and, on the other hand, does not have any influence on testing of the retina center and requires an extremely small apparatus cost.

SUMMARY OF THE INVENTION

This purpose is attained by a method which includes the step of adjusting a testing light point, to which the center of the eye is to be fixated, to a threshold value of the center of the eye of the patient and thereafter repeatedly illuminating this testing light point with the threshold value or a superthreshold value near the threshold (1-4 dB superthreshold) to thereby facilitate control of the fixation during the entire testing interval.

The testing light point which lies in the center is thus, in the inventive method, first adjusted to the threshold value of the patient's eye. This determining of the threshold value of the testing light point which lies in the center, is also necessary in other testing methods when an exact adjusting of the sensitivity of the brightness of the testing light points toward the periphery is to be carried out. During the course of checking the sensitivity of the periphery of the retina according to the invention, the testing light point which lies in the center is repeatedly illuminated at a superthreshold near the threshold (2 dB-4 dB superthreshold) and at irregular intervals. The correct fixation of the patient's eye exists always when this testing light point which lies in the center is recognized. During a deviation of the eye from the fixation position, this testing light point, which is adjusted to the center threshold value, is no longer seen, because the sensitivity drops considerably toward the edge of the retina.

To make the fixation easier and to adjust the testing light point which lies in the center, according to the invention, at least three or four fixation points are provided which are arranged relative to the center testing light point in such a manner that their light rays intersect at the patient's eye, when same is in the intended position. The patient can recognize all three or four testing light points only when his eye is in the position which is predetermined for the measurement. The testing light point which lies in the center is thereafter adjusted to its threshold value, after which the patient can independently check and if necessary correct the exact fixation of the eye during the examination.

In comparison to the presently known methods for controlling the fixation of a patient's eye, the inventive method is distinguished by a very small apparatus cost, because all devices which are needed for this already exist in the perimeter tester. Moreover, maintaining of the exact position is further made easier for the patient through the additional testing light points.

DETAILED DESCRIPTION

Figure 1:
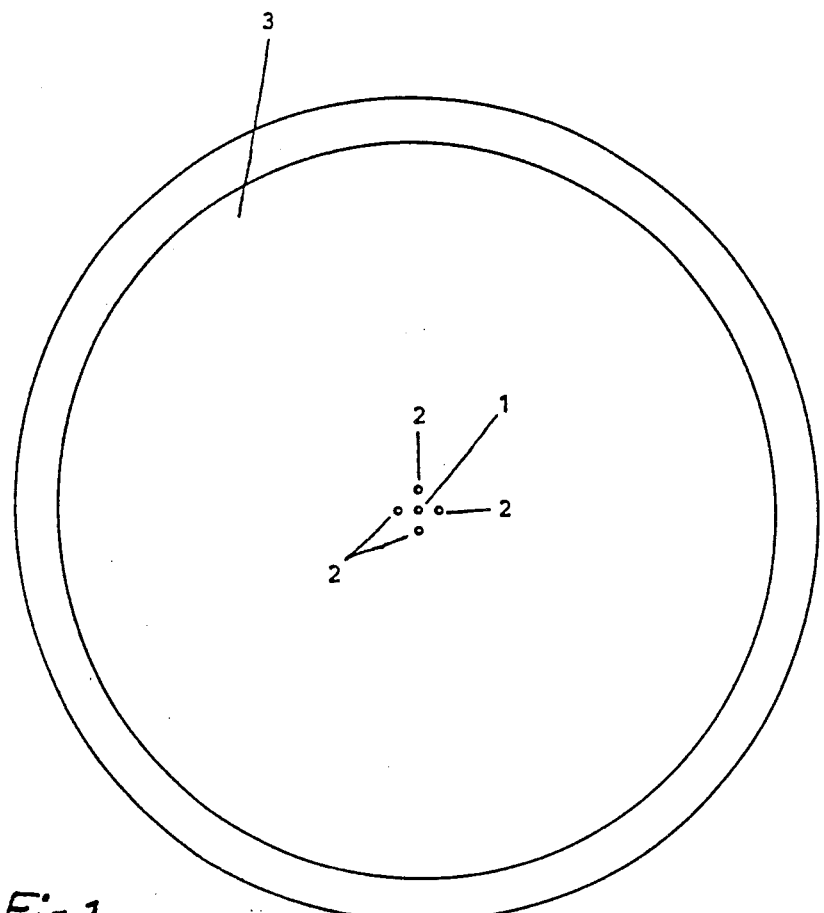
FIG. 1 is an elevational front view of a preferred apparatus for carrying out the inventive method.
Figure 2:
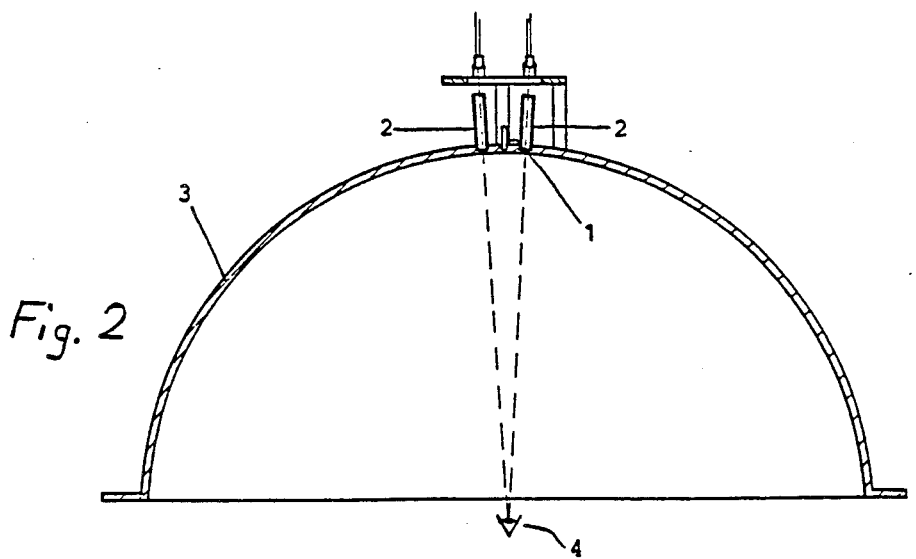
FIG. 2 is a sectional top view of the apparatus of FIG. 1.

In FIGS. 1 and 2, which are respectively a front view and a sectional top view of the screen 3 of a perimeter device, only a center testing light point 1 and four testing points 2 are shown in the screen 3, which serve to control the fixation for the patient. The other testing light points are not illustrated, but they lie in a conventional manner at scattered locations on the screen surface of the perimeter device. As can be seen from FIG. 2, the testing points 2 are arranged so that the lines along which their light rays travel intersect at the eye of the patient 4. The patient has correctly positioned his eye when he can see all four testing points 2 simultaneously. Illumination of the centrally positioned testing light point 1 with a brightness at or near a threshold value then occurs at irregular intervals, which permits a control of the fixation by the operator.

The embodiments of the invention in which an exclusive property or privilege is claimed are defined as follows:

1. In a method for controlling the fixation of the eye of a patient during a measuring of the sensitivity of the retina of the eye using a perimeter device in which a plurality of spaced testing light points of adjustable brightness are visible to the eye of the patient, the improvement comprising the steps of adjusting a central testing light point, to be fixated upon by the patient, to a threshold value of the center of the eye of the patient and thereafter repeatedly illuminating this testing light point with the threshold value or a superthreshold value near the threshold (1-4 dB superthreshold) to facilitate control of the fixation during the entire examination.

2. The method according to claim 1, including the step of providing at least three additional, constantly illuminated testing points which are arranged around the central testing light point and which are oriented so that their rays interact at the location at which the eye to be tested is to be positioned.

3. The method according to claim 2, wherein four of said additional testing points are provided and are arranged symmetrically about the central testing light point.

* * * * *